(12) United States Patent
Sasaki et al.

(10) Patent No.: US 10,726,740 B2
(45) Date of Patent: Jul. 28, 2020

(54) IMAGE PROCESSING DEVICE AND IMAGE PROCESSING METHOD

(71) Applicant: SONY CORPORATION, Tokyo (JP)

(72) Inventors: Toshiyuki Sasaki, Tokyo (JP);
Takahiro Nagano, Kanagawa (JP);
Masatoshi Yokokawa, Kanagawa (JP);
Takefumi Nagumo, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 304 days.

(21) Appl. No.: 15/540,312

(22) PCT Filed: Oct. 9, 2015

(86) PCT No.: PCT/JP2015/078801
§ 371 (c)(1),
(2) Date: Jun. 28, 2017

(87) PCT Pub. No.: WO2016/113963
PCT Pub. Date: Jul. 21, 2016

(65) Prior Publication Data
US 2017/0352290 A1 Dec. 7, 2017

(30) Foreign Application Priority Data

Jan. 15, 2015 (JP) .................................. 2015-006041

(51) Int. Cl.
*G09B 21/00* (2006.01)
*A61B 5/01* (2006.01)
(Continued)

(52) U.S. Cl.
CPC ............ *G09B 21/00* (2013.01); *A61B 5/0075* (2013.01); *A61B 5/0077* (2013.01); *A61B 5/01* (2013.01);
(Continued)

(58) Field of Classification Search
None
See application file for complete search history.

(56) References Cited

U.S. PATENT DOCUMENTS

| 6,055,048 A * | 4/2000 | Langevin ............... A61H 3/061 |
| | | 356/237.1 |
| 2002/0191011 A1* | 12/2002 | Rasouli ................... G06F 3/011 |
| | | 715/702 |

(Continued)

FOREIGN PATENT DOCUMENTS

| JP | 2002-502631 A | 1/2002 |
| JP | 2011-180678 A | 9/2011 |

(Continued)

OTHER PUBLICATIONS

International Search Report and Written Opinion of PCT Application No. PCT/JP2015/078801, dated Dec. 28, 2015, 01 pages of English Translation and 06 pages of ISRWO.

(Continued)

*Primary Examiner* — Kaitlin A Retallick
(74) *Attorney, Agent, or Firm* — Chip Law Group

(57) ABSTRACT

Provided is an image processing device including an infrared image acquisition unit that acquires an infrared image of an imaged object, a visible light image acquisition unit that acquires a visible light image of the imaged object, a generation unit that generates cutaneous sensation control parameters on the basis of the infrared image acquired by the infrared image acquisition unit, and a data processing unit that associates the visible light image acquired by the visible light image acquisition unit with the cutaneous sensation control parameters generated by the generation unit.

7 Claims, 13 Drawing Sheets

(51) Int. Cl.
    *A61B 5/00* (2006.01)
    *H04N 5/33* (2006.01)
    *G06F 3/03* (2006.01)
    *G06F 3/01* (2006.01)
    *H04N 5/247* (2006.01)
    *G06T 7/13* (2017.01)
    *G06T 7/40* (2017.01)

(52) U.S. Cl.
    CPC .............. *A61B 5/015* (2013.01); *A61B 5/486* (2013.01); *A61B 5/7455* (2013.01); *G06F 3/011* (2013.01); *G06F 3/016* (2013.01); *G06F 3/0304* (2013.01); *G06T 7/13* (2017.01); *G06T 7/40* (2013.01); *G09B 21/003* (2013.01); *H04N 5/247* (2013.01); *H04N 5/33* (2013.01); *H04N 5/332* (2013.01); *G06T 2207/10048* (2013.01)

(56) References Cited

U.S. PATENT DOCUMENTS

| | | | |
|---|---|---|---|
| 2010/0151426 A1* | 6/2010 | Tachi | G09B 21/006 434/113 |
| 2015/0080072 A1* | 3/2015 | Kim | A63F 13/213 463/7 |
| 2017/0372497 A1* | 12/2017 | Hu | G06T 11/006 |

FOREIGN PATENT DOCUMENTS

| | | |
|---|---|---|
| JP | 2012-133678 A | 7/2012 |
| JP | 2013-510329 A | 3/2013 |
| JP | 2014-130525 A | 7/2014 |
| JP | 2014-165706 A | 9/2014 |
| WO | 2007/66717 A1 | 6/2007 |
| WO | 2007/066717 A1 | 6/2017 |

OTHER PUBLICATIONS

Office Action for JP Patent Application No. 2016-569226, dated Oct. 1, 2019, 3 pages of Office Action and 3 pages of English Translation.

* cited by examiner

FIG.11

| PIXEL | FREQUENCY | DURATION TIME |
|---|---|---|
| C1~C9 | F1 | T1 |
| C10~C18 | F2 | T1 |
| C19~C27 | F3 | T1 |
| C28~C36 | F4 | T1 |
| C37~C45 | F5 | T2 |
| C46~C54 | F6 | T2 |
| C55~C63 | F7 | T2 |
| C64~C72 | F8 | T2 |
| ⋮ | ⋮ | ⋮ |

IMAGE PROCESSING DEVICE AND IMAGE PROCESSING METHOD

CROSS REFERENCE TO RELATED APPLICATIONS

This application is a U.S. National Phase of International Patent Application No. PCT/JP2015/078801 filed on Oct. 9, 2015, which claims priority benefit of Japanese Patent Application No. JP 2015-006041 filed in the Japan Patent Office on Jan. 15, 2015. Each of the above-referenced applications is hereby incorporated herein by reference in its entirety.

TECHNICAL FIELD

The present invention relates to an image processing device, an image processing method, and a program.

BACKGROUND ART

In recent years, a technology for controlling a cutaneous sensation has been developed as a technology for delivering information to a user. In particular, it is possible to achieve smooth information delivery to elderly people and the like whose visual functions have diminished by controlling a cutaneous sensation while displaying an image.

For example, Patent Literature 1 discloses a technology for adding a function of controlling a tactile sensation through electrical stimulation by controlling a voltage to be applied to counter electrodes arranged in a grid shape in a display apparatus that displays images.

Also, Patent Literature 2 discloses a technology for controlling a temperature sensation through temperature stimulation by controlling a current to be applied to Peltier devices arranged in a grid shape.

CITATION LIST

Patent Literature

Patent Literature 1: JP 2014-130525A
Patent Literature 2: JP 2011-180678A

DISCLOSURE OF INVENTION

Technical Problem

However, it is difficult for the technology for controlling a cutaneous sensation while displaying an image to reduce a human load for a cutaneous sensation control setting corresponding to displayed images. For example, the technology disclosed in Patent Literature 1 requires a voltage value to be manually set corresponding to the displayed images.

Thus, the present disclosure proposes a novel and improved image processing device, an image processing method, and a program capable of reducing a human load for a cutaneous sensation control setting corresponding to an image.

Solution to Problem

According to the present disclosure, there is provided an image processing device including: an infrared image acquisition unit that acquires an infrared image of an imaged object; a visible light image acquisition unit that acquires a visible light image of the imaged object; a generation unit that generates cutaneous sensation control parameters on the basis of the infrared image acquired by the infrared image acquisition unit; and a data processing unit that associates the visible light image acquired by the visible light image acquisition unit with the cutaneous sensation control parameters generated by the generation unit.

Further, according to the present disclosure, there is provided an image processing method including: acquiring an infrared image of an imaged object by an image processing device; acquiring a visible light image of the imaged object; generating cutaneous sensation control parameters on the basis of the acquired infrared image; and associating the acquired visible light image with the generated cutaneous sensation control parameters.

Further, according to the present disclosure, there is provided a program causing a computer that controls an image processing device to function as: an infrared image acquisition unit that acquires an infrared image of an imaged object; a visible light image acquisition unit that acquires a visible light image of the imaged object; a generation unit that generates cutaneous sensation control parameters on the basis of the infrared image acquired by the infrared image acquisition unit; and a data processing unit that associates the visible light image acquired by the visible light image acquisition unit with the cutaneous sensation control parameters generated by the generation unit.

Advantageous Effects of Invention

According to the present disclosure, it is possible to reduce a human load for a cutaneous sensation control setting corresponding to an image.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 11 is an explanatory diagram illustrating a specific example of a data table in which visible light images and tactile sensation control parameters are associated.

MODE(S) FOR CARRYING OUT THE INVENTION

Figure 1:
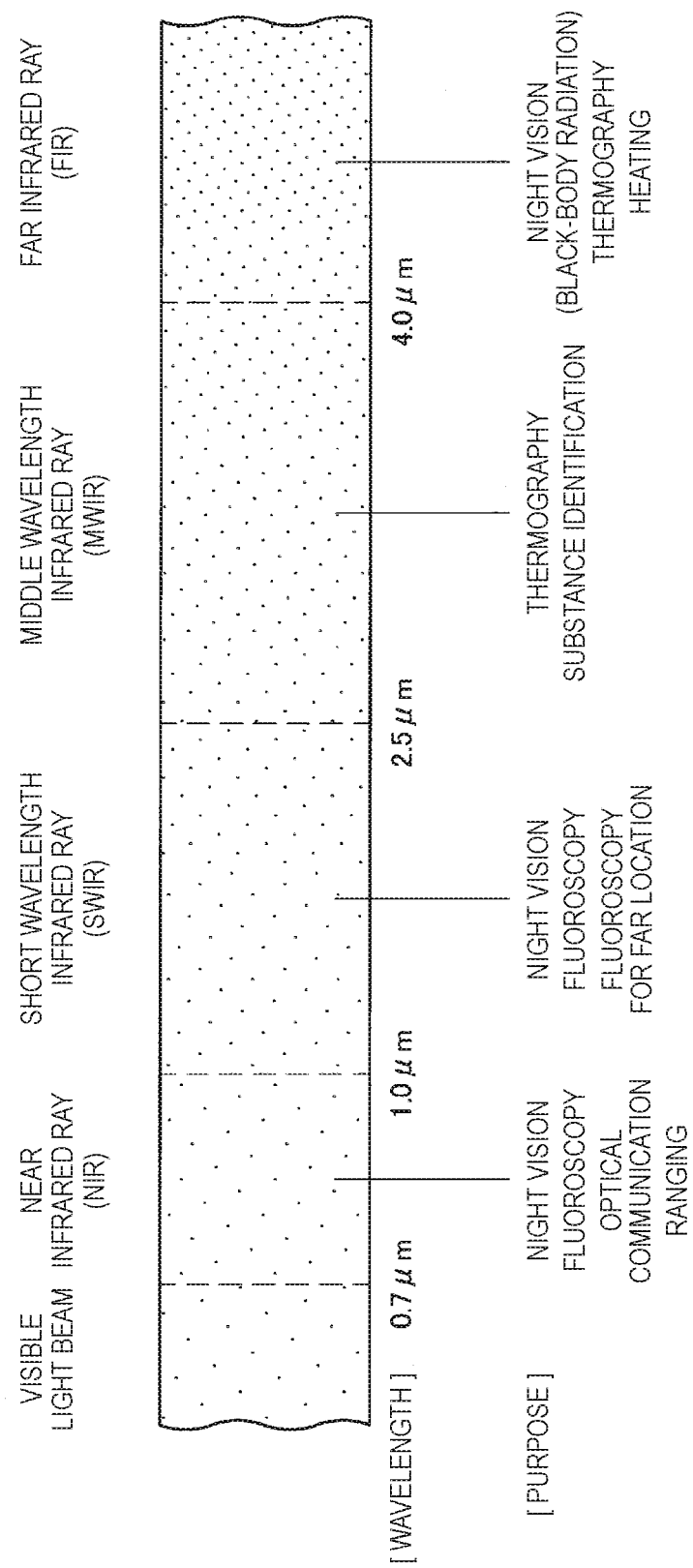
FIG. 1 is an explanatory diagram illustrating various purposes of infrared (IR) images that depend on wavelengths.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description will be given in the following order.
1. Introduction
2. Image processing device according to embodiment of present disclosure
2-1. Hardware configuration
2-2. Functional configuration
2-3. Operations
2-4. Advantages
2-5. Modification example
2-6. Application example
3. Conclusion <1. Introduction>

FIG. 1 is an explanatory diagram illustrating various purposes of infrared (IR) images depending on wavelengths. The horizontal direction in FIG. 1 corresponds to a wavelength of an infrared ray, and the wavelength increases from the left side to the right side. A light beam with a wavelength of equal to or less than 0.7 µm is a visible light beam, and human vision senses this visible light beam. An infrared ray with a wavelength within a range from 0.7 µm to 1.0 µm is classified into a near infrared ray (NIR). The near infrared ray can be used for night vision, fluoroscopy, optical communication, and ranging. An infrared ray with a wavelength within a range from 1.0 µm to 2.5 µm is classified into a short wavelength infrared ray (SWIR). The short wavelength infrared ray can also be used for night vision and fluoroscopy. A night vision device that uses a near infrared ray or a short wavelength infrared ray emits an infrared ray to the vicinity first, and receives reflected light thereof, thereby obtaining an infrared image. An infrared ray with a wavelength within a range from 2.5 µm to 4.0 µm is classified into a middle wavelength infrared ray (MWIR). Since an absorption spectrum unique to a substance appears within the wavelength range of the middle wavelength infrared ray, the middle wavelength infrared ray can be used for identifying substances. The middle wavelength infrared ray can also be used for thermography. An infrared ray with a wavelength of equal to or greater than 4.0 µm is classified into a far infrared ray (FIR). The far infrared ray can be used for night vision, thermography, and heating. An infrared ray emitted by black-body radiation from a substance corresponds to the far infrared ray. Therefore, a night vision device that uses a far infrared ray can obtain an infrared image by capturing black-body radiation from a substance without emitting an infrared ray. The boundary values of the ranges of the wavelengths illustrated in FIG. 1 are only examples. There are various definitions for boundary values of classifying the infrared rays, and advantages of the technology according to the present disclosure, which will be described later, can be achieved under any definitions.

As described above, in particular, an infrared camera that captures an NIR image or an SWIR image typically emits infrared rays for capturing images. Here, it is known that reflected light intensity properties of a surface of an object with respect to angles of light emitted toward the surface of the object depend on a surface roughness of the object. In this specification, a mechanism capable of reducing a human load for a cutaneous sensation control setting corresponding to an image by, for example, utilizing such properties of light will be described in detail.

<2. Image Processing Device According to Embodiment of Present Disclosure>

First, an image processing device 10 according to an embodiment of the present disclosure will be described.

[2-1. Hardware Configuration]

Figure 2:
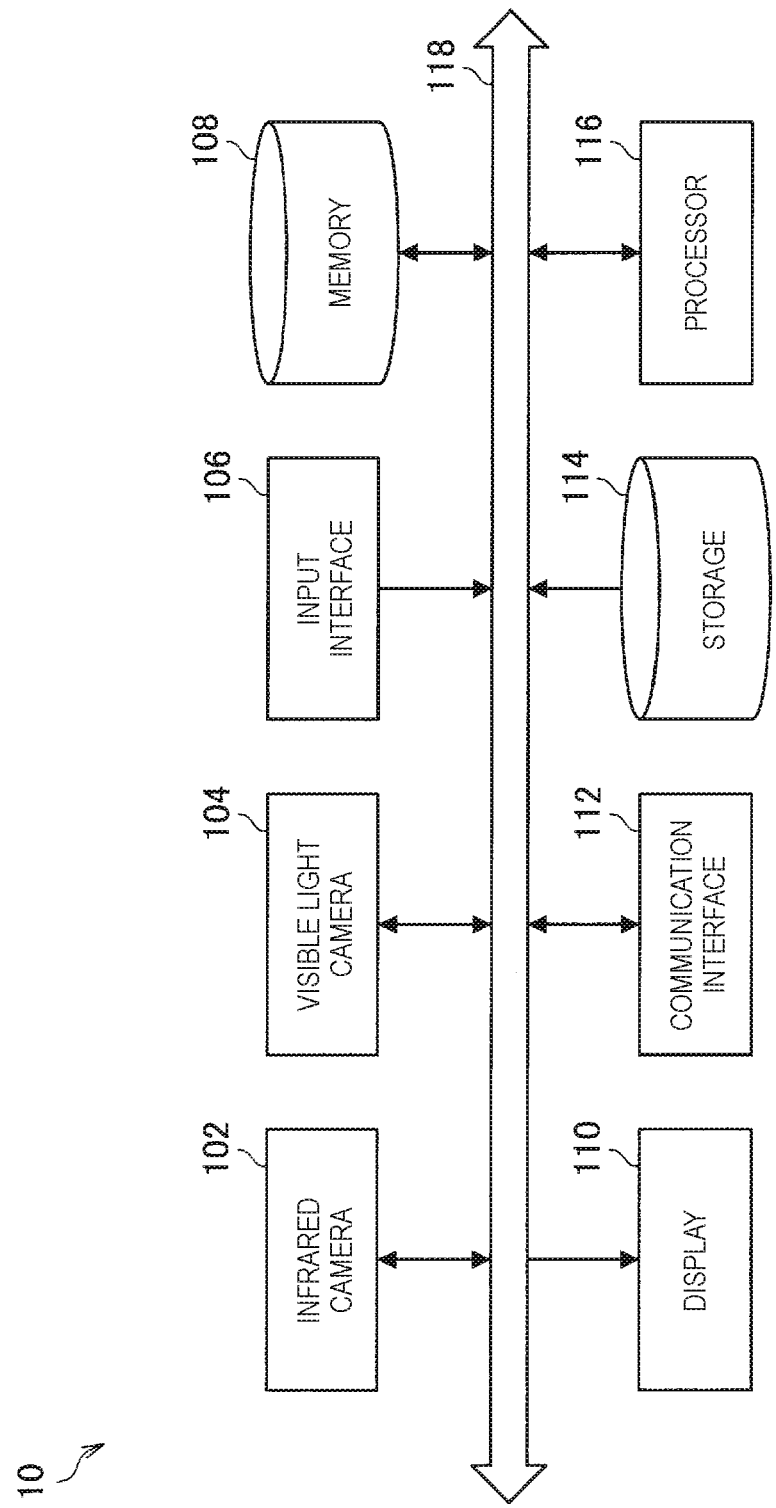
FIG. 2 is an explanatory diagram illustrating a specific example of a hardware configuration of an image processing device according to an embodiment of the present disclosure.

FIG. 2 is an explanatory diagram illustrating a specific example of a hardware configuration of the image processing device 10 according to the embodiment of the present disclosure. As illustrated in FIG. 2, the image processing device 10 includes an infrared camera 102, a visible light camera 104, an input interface 106, a memory 108, a display 110, a communication interface 112, a storage 114, a processor 116, and a bus 118.

(Infrared Camera)

The infrared camera 102 is an imaging module that performs image capturing by using infrared rays and obtains an infrared image. The infrared camera 102 has an array of imaging elements that sense infrared rays. If the infrared camera 102 obtains an NIR image or an SWIR image by image capturing, the infrared camera 102 may have a light emitting element that emits infrared rays with wavelengths corresponding to the NIR image or the SWIR image. For example, the infrared camera 102 obtains infrared images by emitting infrared rays periodically or in response to a trigger such as a user input and capturing infrared rays reflected by an imaged object or a background thereof. A series of infrared images obtained by the infrared camera 102 may form a movie image. The imaging elements may be able to detect visible light in addition to the infrared rays, and in such a case, the visible light camera 104 can be omitted from the configuration of the image processing device 10.

Figure 3:
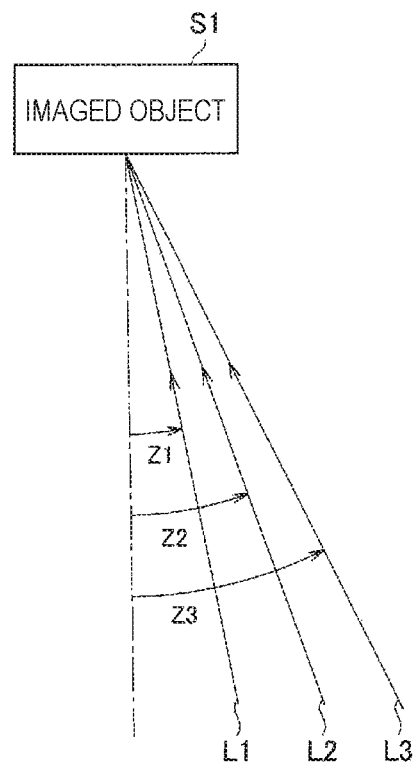
FIG. 3 is an explanatory diagram illustrating specific examples of a plurality of infrared ray irradiation angles with respect to an imaged object.

Also, a position of the light emitting element in the infrared camera 102 is variably controlled by the processor 116. Therefore, it is possible to obtain a plurality of infrared images at different infrared ray irradiation angles with respect to an imaged object. For example, it is possible to obtain a plurality of infrared images at different infrared ray irradiation angles with respect to an imaged object by controlling the position of the light emitting element in the infrared camera 102 to be at a preset position for each frame. As illustrated in FIG. 3, for example, an infrared ray irradiation angle corresponding to an infrared ray L1 emitted from the light emitting element toward an imaged object S1 in a certain frame is an angle Z1, an infrared ray irradiation angle corresponding to an infrared ray L2 emitted from the light emitting element toward the imaged object S1 in the following frame is an angle Z2, and an infrared ray irradiation angle corresponding to an infrared ray L3 emitted from the light emitting element toward the imaged object S1 in the frame after that is an angle Z3. The technical scope of the present disclosure is not limited to an example in which the position of the light emitting element in the infrared camera 102 is automatically controlled, and for example, the position of the light emitting element in the infrared camera 102 may be manually controlled.

(Visible Light Camera)

The visible light camera 104 is an imaging module that performs image capturing by using visible light and obtains visible light images. The visible light camera 104 has an array of imaging elements that sense visible light with different wavelengths. For example, the visible light camera 104 may have an alignment of imaging elements that have sensitivity ranges in a red region, a green region, and a blue region.

(Input Interface)

The input interface 106 is used by a user to operate the image processing device 10 or input information to the image processing device 10. For example, the input interface 106 may include an input device such as a touch sensor, a button, or a switch. The input interface 106 may include a microphone for sound input and sound recognition module. The input interface 106 may include a remote control module that receives commands selected by the user from a remote device.

(Memory)

The memory 108 is a storage medium that can include a random access memory (RAM) and a read only memory (ROM). The memory 108 is coupled to the processor 116 and stores a program and data for processing executed by the processor 116.

(Display)

The display 110 is a display module that has a screen for displaying an image. For example, the display 110 may be a liquid crystal display (LCD), an organic light-emitting diode (OLED), or a cathode ray tube (CRT).

(Communication Interface)

The communication interface 112 is a module that relays communication between the image processing device 10 and other devices. The communication interface 112 establishes communication connection in accordance with an arbitrary wireless communication protocol or a wired communication protocol.

(Storage)

The storage 114 is a storage device that accumulates image data that can include infrared images and visible light images or stores a database that can be used in infrared image processing. The storage 114 embeds a storage medium such as a semiconductor memory or hard disk therein. The program and the data described in the specification may be acquired from a data source (a data server, a network storage, or an external memory, for example) outside the image processing device 10.

(Processor)

The processor 116 is a processing module such as a central processing unit (CPU) or a digital signal processor (DSP). The processor 116 causes a function for reducing a human load in a cutaneous sensation control setting corresponding to an image to operate by executing a program stored in the memory 108 or another storage medium.

(Bus)

The bus 118 connects the infrared camera 102, the visible light camera 104, the input interface 106, the memory 108, the display 110, the communication interface 112, the storage 114, and the processor 116 to each other.

[2-2. Functional Configuration]

In the previous section, the hardware configuration of the image processing device 10 according to the embodiment of the present disclosure was described. Next, a logical functional configuration of the image processing device 10 according to the embodiment of the present disclosure will be described with reference to FIG. 4.

Figure 4:
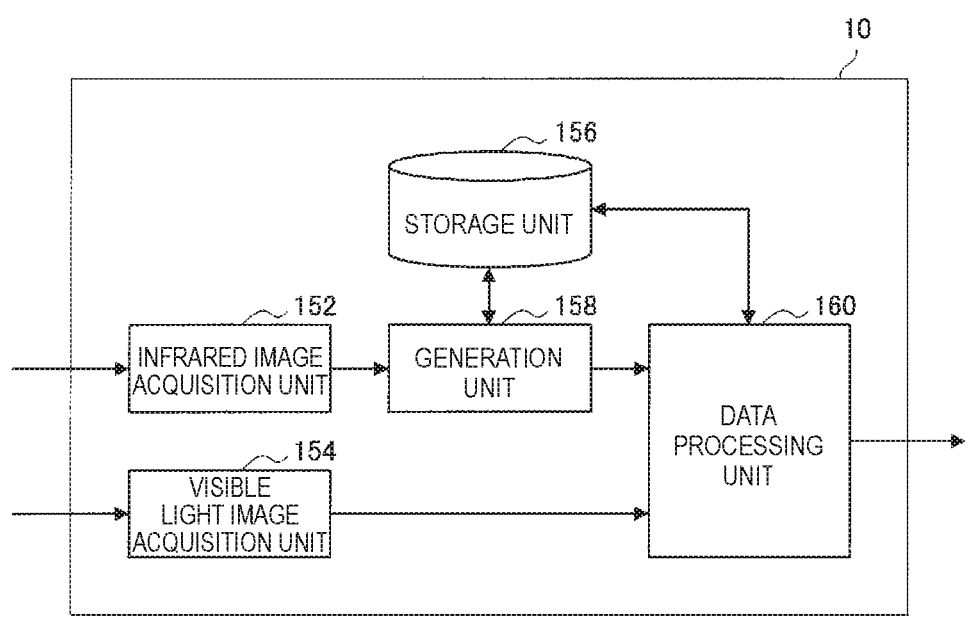
FIG. 4 is an explanatory diagram illustrating a specific example of a logical functional configuration of the image processing device according to the embodiment of the present disclosure.

FIG. 4 is a block diagram illustrating an example of a configuration of a theoretical function realized by components in the image processing device 10 illustrated in FIG. 2 being in cooperation with each other. As illustrated in FIG. 4, the image processing device 10 includes an infrared image acquisition unit 152, a visible light image acquisition unit 154, a storage unit 156, a generation unit 158, and a data processing unit 160.

(Infrared Image Acquisition Unit)

The infrared image acquisition unit 152 acquires an infrared image of an imaged object at each of a plurality of infrared ray irradiation angles with respect to the imaged object and outputs the acquired infrared image to the generation unit 158. For example, the infrared image acquisition unit 152 may acquire an infrared image obtained by the infrared camera 102. The infrared image acquisition unit 152 may acquire an infrared image stored in the storage 114. The infrared image acquisition unit 152 may acquire an infrared image from another device via the communication interface 112. The infrared image acquired by the infrared image acquisition unit 152 may be an image that has undergone preliminary processing such as signal amplification and noise removal. The infrared image acquisition unit 152 may decode an infrared image from a coded stream compressed and encoded.

(Visible Light Image Acquisition Unit)

The visible light image acquisition unit 154 acquires a visible light image of an imaged object and outputs the acquired visible light image to the data processing unit 160. For example, the visible light image acquisition unit 154 may acquire a visible light image obtained by the visible light camera 104. Also, the visible light image acquisition unit 154 may acquire a visible light image stored in the storage 114. The visible light image acquisition unit 154 may acquire a visible light image from another apparatus via the communication interface 112. The visible light image acquired by the visible light image acquisition unit 154 may be an image that has undergone preliminary processing such as signal amplification and noise removal. The visible light image acquisition unit 154 may decode a visible light image from a compressed coded stream. If the infrared camera 102 includes an imaging element capable of detecting visible light and can capture a visible light image, the visible light image acquisition unit 154 may acquire the visible light image obtained by the infrared camera 102.

(Storage Unit)

The storage unit 156 stores data to be referred to by the generation unit 158 for cutaneous sensation control parameter generation processing as well as visible light images and cutaneous sensation control parameters associated with the data processing unit 160.

(Generation Unit)

The generation unit 158 generates cutaneous sensation control parameters on the basis of an infrared image input from the infrared image acquisition unit 152, and outputs the generated cutaneous sensation control parameters to the data processing unit 160. The cutaneous sensation control parameters are parameter used for controlling a cutaneous sensation. For example, the cutaneous sensation control parameters generated by the generation unit 158 include tactile sensation control parameters. Furthermore, the tactile sensation control parameters generated by the generation unit 158 include a parameter for controlling a tactile sensation corresponding to a surface roughness of an object and a parameter for controlling a tactile sensation corresponding to a density of texture boundaries on a surface of the object.

Generally, it is difficult to let a human perceive the presence of a texture boundary on a surface of an object in a section having a density of the texture boundaries on the surface of the object equal to or greater than a specific value merely by letting the person perceive a surface roughness of the object for each texture. Therefore, it is possible to let a human sense the presence of the texture boundary on the surface of the object without depending on the density of the texture boundaries on the surface of the object by controlling a tactile sensation corresponding to the density of the texture boundaries on the surface of the object.

Figure 5:
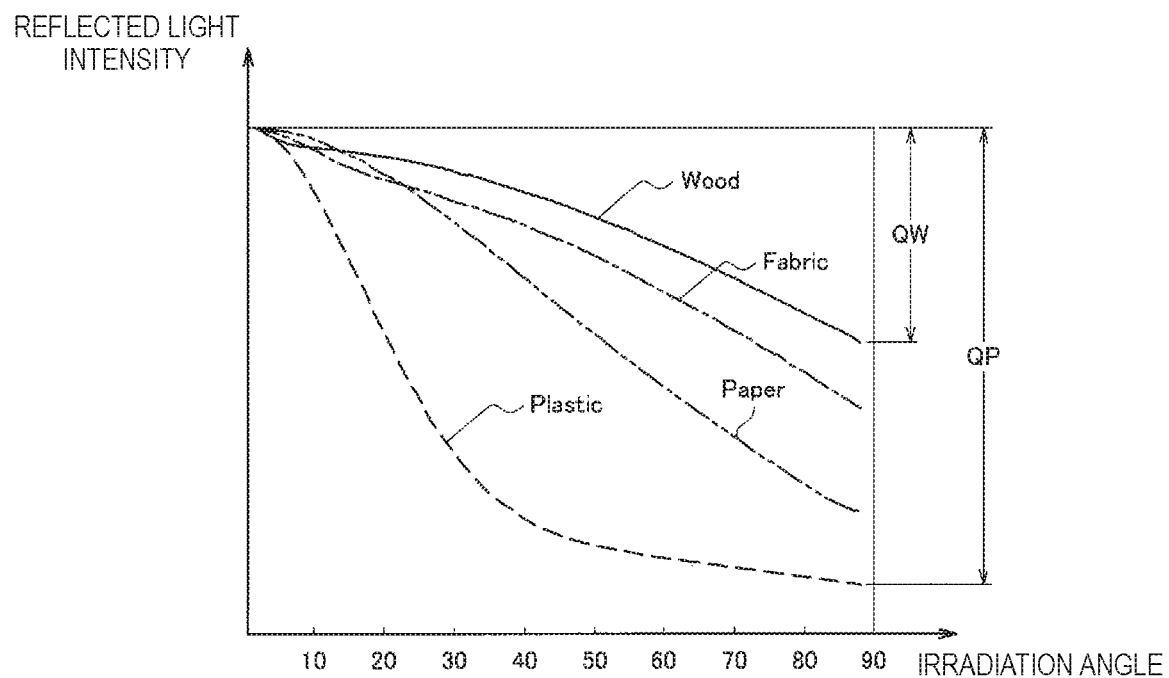
FIG. 5 is an explanatory diagram illustrating a specific example of a reflected light intensity property of each substance with respect to each light irradiation angle.

Here, it is known that reflected light intensity properties of a surface of an object with respect to angles of light emitted toward the surface of the object depends on a surface roughness of the object. The graph in FIG. 5 illustrates a reflected light intensity properties of each of plastic, paper, fiber, and wood in a normal direction of a surface of an object with respect to a light irradiation angle in one example. As illustrated in FIG. 5, a change in a reflected light intensity in the normal direction of the surface of the object that accompanies a change in the irradiation angle increases as a surface roughness of a substance decreases. For example, since a surface roughness of a plastic object is smaller than a surface roughness of a wood object, a dynamic range QP of a reflected light intensity of the plastic at a plurality of irradiation angles is greater than a dynamic range QW of a reflected light intensity of the wood at the plurality of irradiation angles.

The generation unit 158 in the embodiment of the present disclosure utilizes such properties of light, and generates tactile sensation control parameters on the basis of pixel values of the infrared image acquired by the infrared image acquisition unit 152. For example, the generation unit 158 generates the tactile sensation control parameters on the basis of a plurality of infrared images that are obtained at a plurality of infrared ray irradiation angles with respect to an imaged object.

Specifically, the generation unit 158 estimates a surface roughness of the object on the basis of the plurality of infrared images that are obtained at the plurality of infrared ray irradiation angles. Also, the generation unit 158 estimates a density of texture boundaries on a surface of the object on the basis of the estimated surface roughness of the object. Then, the generation unit 158 generates a parameter for controlling a tactile sensation corresponding to the estimated surface roughness of the object and a parameter for controlling a tactile sensation corresponding to the estimated density of the texture boundaries on the surface of the object. Hereinafter, a specific example of the tactile sensation control parameter generation processing performed by the generation unit 158 will be described.

Figure 6:
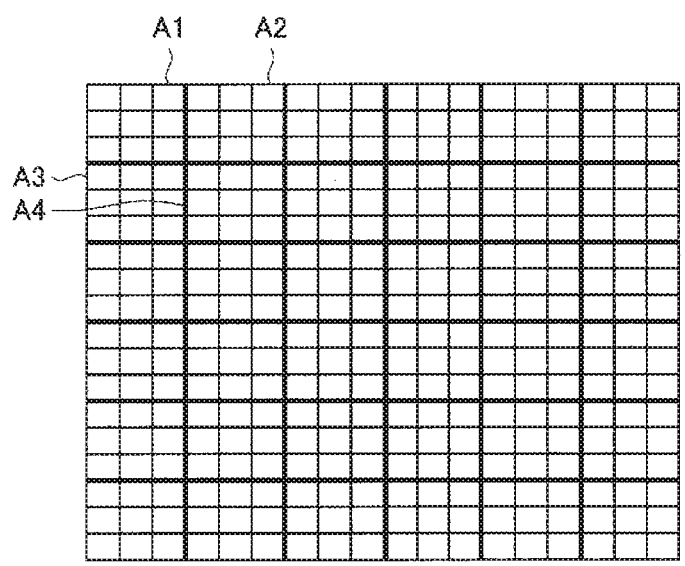
FIG. 6 is an explanatory diagram illustrating a specific example of division into pixel regions in an estimation of a surface roughness of a substance.

The generation unit 158 estimates a surface roughness of an object for each pixel region of an infrared image. FIG. 6 is an explanatory diagram illustrating a specific example of division into pixel regions in an estimation of a surface roughness of an object. In the estimation of the surface roughness of the object, an infrared image acquired by the infrared image acquisition unit 152 is divided into, for example, 3×3 pixel regions as illustrated in FIG. 6. FIG. 6 illustrates pixel regions A1 to A4 obtained by dividing the infrared image in one example. In one example of processing in the estimation of the surface roughness of the object, the generation unit 158 first determines a pixel region of interest and estimates a surface roughness of the object in the determined pixel region of interest. Then, the generation unit 158 determines a pixel region for which the estimation of the surface roughness of the object is not completed as the pixel region of interest. The generation unit 158 estimates the surface roughness of the object in all of the pixel regions by repeating a determination of a pixel region of interest and estimation of surface roughness of the object as described above.

Specifically, the generation unit 158 first determines a pixel region A1 as a pixel region of interest and estimates a surface roughness of the object in the pixel region A1. The generation unit 158 estimates the surface roughness of the object in the pixel region A1 on the basis of a distribution of pixel values corresponding to the pixel region A1 at a plurality of infrared ray irradiation angles. For example, the generation unit 158 estimates the surface roughness of the object in the pixel region A1 on the basis of a dynamic range of an average pixel value in the pixel region A1 at the plurality of infrared ray irradiation angles.

Figure 7:
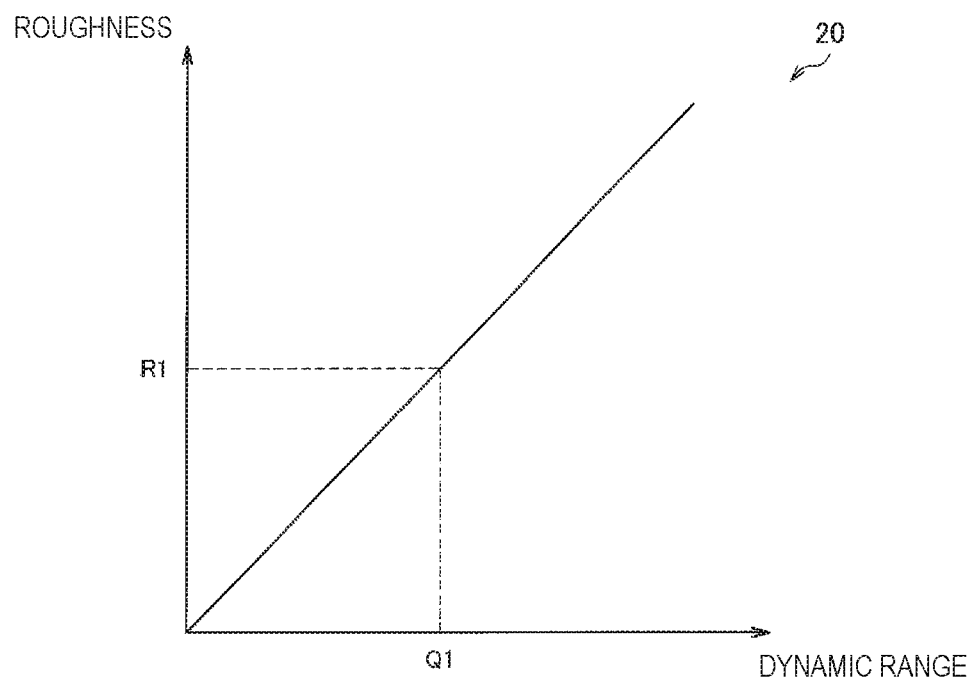
FIG. 7 is an explanatory diagram illustrating a specific example of a correlation model between a dynamic range of pixel values at a plurality of infrared ray irradiation angles and a surface roughness of the object.

FIG. 7 is an explanatory diagram illustrating a specific example of a correlation model 20 between a dynamic range of pixel values at a plurality of infrared ray irradiation angles and a surface roughness of an object. FIG. 7 illustrates a surface roughness corresponding to each of dynamic ranges of pixel values at a plurality of infrared ray irradiation angles. The generation unit 158 acquires the correlation model 20 stored in the storage unit 156 and estimates the surface roughness of the object in the pixel region A1 corresponding to a dynamic range Q1 of an average pixel value in the pixel region A1 at the plurality of infrared ray irradiation angles as roughness R1 by using the acquired correlation model 20. Similarly, the generation unit 158 estimates a surface roughness of the object in pixel regions A2 to A4 and pixel regions other than A1 to A4 in FIG. 6. The generation unit 158 may estimate a surface roughness of the object for each pixel of the infrared image.

Figure 8:
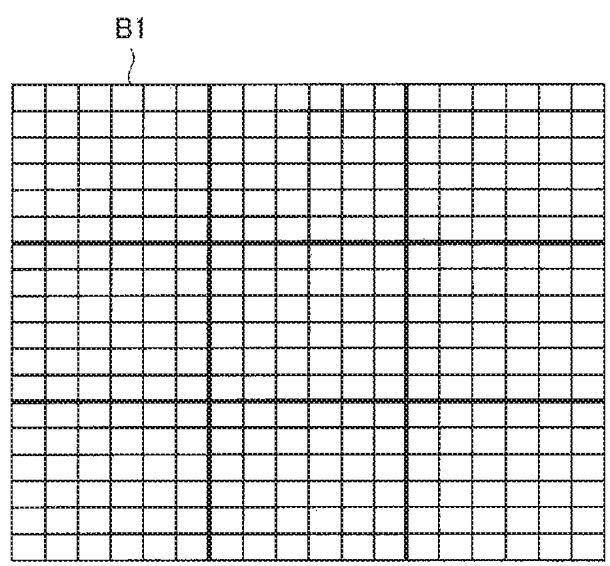
FIG. 8 is an explanatory diagram illustrating a specific example of division into pixel regions in an estimation of density of texture boundaries.

Also, the generation unit 158 estimates a density of texture boundaries on a surface of the object for each pixel region of the infrared image. In the estimation of the density of the texture boundaries, the infrared image acquired by the infrared image acquisition unit 152 is divided into a plurality of pixel regions that are obtained by dividing the infrared image in the estimation of the surface roughness of the object. FIG. 8 is an explanatory diagram illustrating a specific example of division into pixel regions in an estimation of a density of texture boundaries. In the estimation of the density of the texture boundaries, the infrared image acquired by the infrared image acquisition unit 152 is divided into, for example, 6×6 pixel regions as illustrated in FIG. 8. FIG. 8 illustrates a pixel region B1 obtained by dividing an infrared image in one example. The pixel region B1 illustrated in FIG. 8 includes the pixel regions A1 to A4 obtained by dividing the infrared image in the estimation of the surface roughness of the object as illustrated in FIG. 6. In one example of processing in the estimation of the density of the texture boundaries on the surface of the object, the generation unit 158 first determines a pixel region of interest and estimates a density of texture boundaries in the determined pixel region of interest. Then, the generation unit 158 determines a pixel region for which the estimation of the density of the texture boundaries is completed as a pixel region of interest. The generation unit 158 estimates the density of the texture boundaries on the surface of the object in all of the pixel regions by repeating the determination of the pixel region of interest and the estimation of the density of the texture boundaries.

Specifically, the generation unit 158 first determines the pixel region B1 as the pixel region of interest and estimates a density of the texture boundaries in the pixel region B1. The generation unit 158 estimates the density of the texture boundaries on the surface of the object on the basis of a dispersion of estimated surface roughnesses of the object. For example, the generation unit 158 estimates the density of the texture boundaries on the surface of the object in the pixel region B1 on the basis of a dispersion of estimated surface roughnesses of the object in the pixel region B1.

Figure 9:
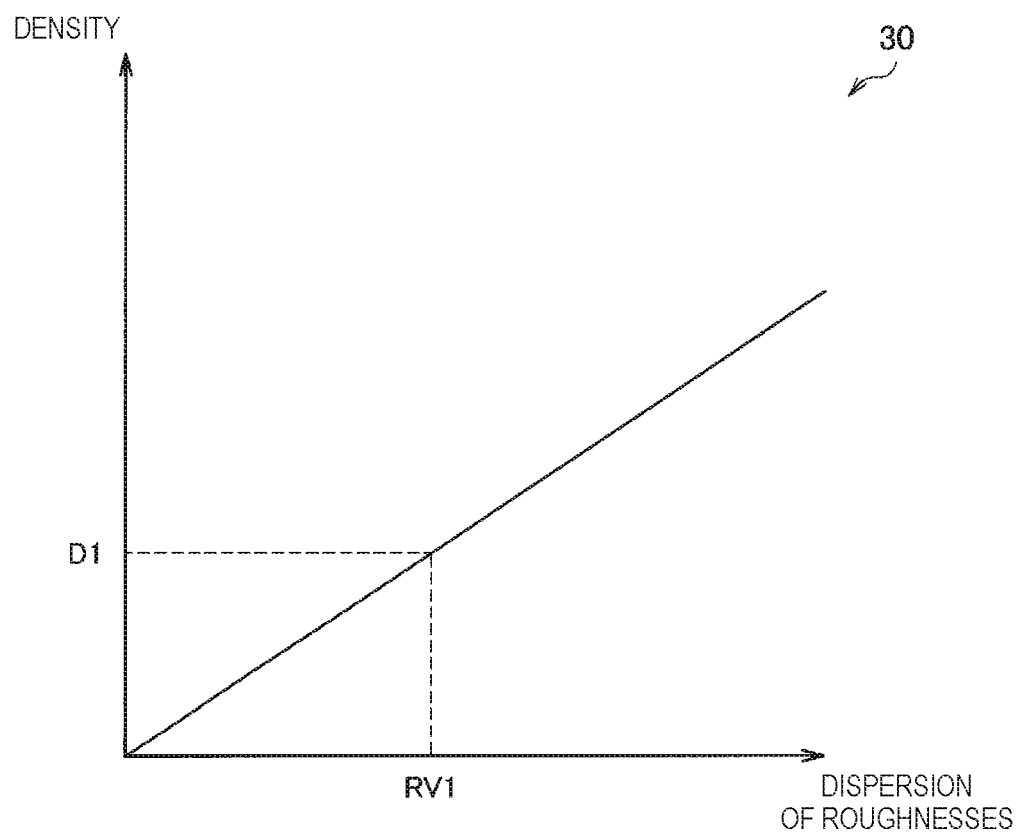
FIG. 9 is an explanatory diagram illustrating a specific example of a correlation model between a dispersion of surface roughnesses of an object and a density of texture boundaries.

FIG. 9 is an explanatory diagram illustrating a specific example of a correlation model 30 between a dispersion of surface roughnesses of an object and a density of texture boundaries. FIG. 9 illustrates the density of the texture boundaries corresponding to the dispersion of the surface roughnesses of the object. The generation unit 158 acquires the correlation model 30 stored in the storage unit 156 and estimates that a density of texture boundaries in the pixel region B1 corresponding to a dispersion RV1 of surface roughnesses of the object in the pixel region B1 is a density D1 by using the acquired correlation model 30. Similarly, the generation unit 158 estimates a density of texture boundaries in pixel regions other than the pixel region B1 in FIG. 8.

Figure 10:
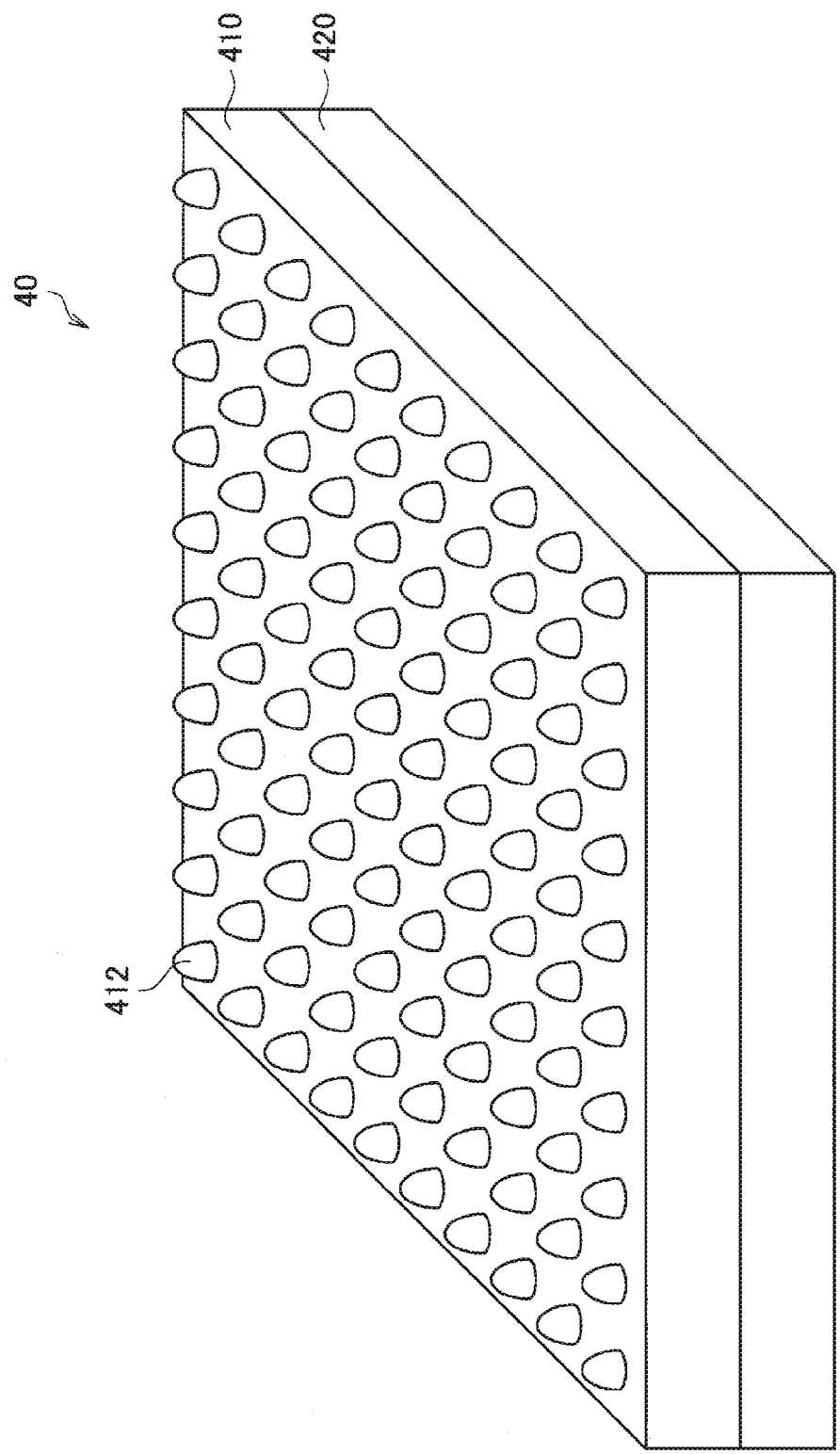
FIG. 10 is an appearance diagram illustrating a first example of a tactile sensation presenting display.

Here, a technology for controlling a tactile sensation through an oscillation stimulation by controlling oscillations that are caused in oscillators arranged in a grid shape is known. FIG. 10 is an appearance diagram illustrating a specific example of a tactile sensation presenting display 40 that uses such a technology. As illustrated in FIG. 10, the tactile sensation presenting display 40 includes a tactile sensation presenting unit 410 that includes oscillators 412 arranged in a grid shape and a display unit 420 that displays an image. An occurrence of oscillations and a stoppage of the oscillations by the oscillators 412 are periodically repeated. Also, the tactile sensation presenting unit 410 causes the oscillator 412 to periodically oscillate. The tactile sensation presenting unit 410 is laminated on the display unit 420 so that the tactile sensation presenting display 40 can control a tactile sensation while displaying an image. Also, it is known that a frequency of oscillations that are caused in the oscillators 412 is correlated with a tactile sensation corresponding to a surface roughness of an object and that a duration time of the oscillations caused in the oscillators 412 is correlated with the tactile sensation corresponding to a density of texture boundaries on a surface of the object in the tactile sensation presenting display 40.

In the example of the present disclosure, the generation unit 158 generates, for example, a value indicating a frequency of oscillations that are caused in the target as a parameter for controlling a tactile sensation corresponding to a surface roughness of an object estimated by the generation unit 158. Also, the generation unit 158 generates, for example, a value indicating a duration time of the oscillations that are caused in the target as a parameter for controlling a tactile sensation corresponding to the density of the texture boundaries on the surface of the object estimated by the generation unit 158. The generation unit 158 may generate the tactile sensation control parameters for each pixel region of an infrared image. For example, the generation unit 158 generates a value indicating the frequency of the oscillations that are caused in the target for each pixel region obtained by the division in the estimation of the surface roughness of the object as illustrated in FIG. 6, and generates a value indicating the duration time of the oscillations that are caused in the target for each pixel region obtained by the division in the estimation of the density of the texture boundaries as illustrated in FIG. 8.

(Data Processing Unit)

The data processing unit 160 associates a visible light image acquired by the visible light image acquisition unit 154 with cutaneous sensation control parameters generated by the generation unit 158. For example, the data processing unit 160 performs association by assigning the cutaneous sensation control parameters to pixels of the visible light image corresponding to each pixel region of the infrared image. Also, the data processing unit 160 causes the storage unit 156 to store the associated visible light image and the cutaneous sensation control parameters. FIG. 11 is an explanatory diagram illustrating a specific example of a data table 50 in which visible light images and tactile sensation control parameters are associated.

Specifically, the value indicating the frequency of the oscillations generated for each pixel region obtained by the division in the estimation of the surface roughness of the object is assigned to the pixels of the visible light image corresponding to each pixel region obtained by the division in the estimation of the surface roughness of the object. For example, if a value F1 indicating a frequency of oscillations is generated for the pixel region A1 in FIG. 6 and pixels C1 to C9 of the visible light image correspond to the pixel region A1, the value F1 indicating the frequency of the oscillations is assigned to the pixels C1 to C9 of the visible light image. Specifically, values F1 to F8 indicating frequencies of oscillations generated for the pixel regions obtained by the division in the estimation of the surface roughness of the object are respectively assigned to pixels C1 to C9, C10 to C18, C19 to C27, C28 to C36, C37 to C45, C46 to C54, C55 to C63, and C64 to C72 of the visible light image in the data table 50 illustrated in FIG. 11.

Also, the value indicating the duration time of the oscillations generated for each pixel region obtained by the division in the estimation of the density of the texture boundaries is assigned to the pixels of the visible light image corresponding to each pixel region obtained by the division in the estimation of the density of the texture boundaries on the surface of the object. For example, if a value T1 indicating a duration time of oscillations is generated for the pixel region B1 in FIG. 8 and pixels C1 to C36 of the visible light image correspond to the pixel region B1, the value T1 indicating the duration time of the oscillations is assigned to the pixels C1 to C36 of the visible light image. Specifically, values T1 and T2 indicating a duration time of oscillations generated for the pixel regions obtained by the division in the estimation of the density of the texture boundaries are respectively assigned to the pixels C1 to 36 and C37 to C72 of the visible light image in the data table 50 illustrated in FIG. 11.

The data processing unit 160 may associate a visible light image obtained at the same timing as a timing of capturing any of the plurality of infrared images used in the tactile sensation control parameter generation processing by the generation unit 158 with the generated tactile sensation control parameters. If, for example, three infrared images obtained by image capturing being performed three times are used in the tactile sensation control parameter generation processing, the data processing unit 160 may associate a visible light image captured at the same timing as a timing at which the second infrared image is captured with the generated tactile sensation control parameters.

[2-3. Operations]

In the previous section, the configuration of a theoretical function of the image processing device 10 according to the embodiment of the present disclosure was described. Next, a flow of processing performed by the image processing device 10 according to the embodiment of the present disclosure will be described with reference to FIG. 12.

Figure 12:
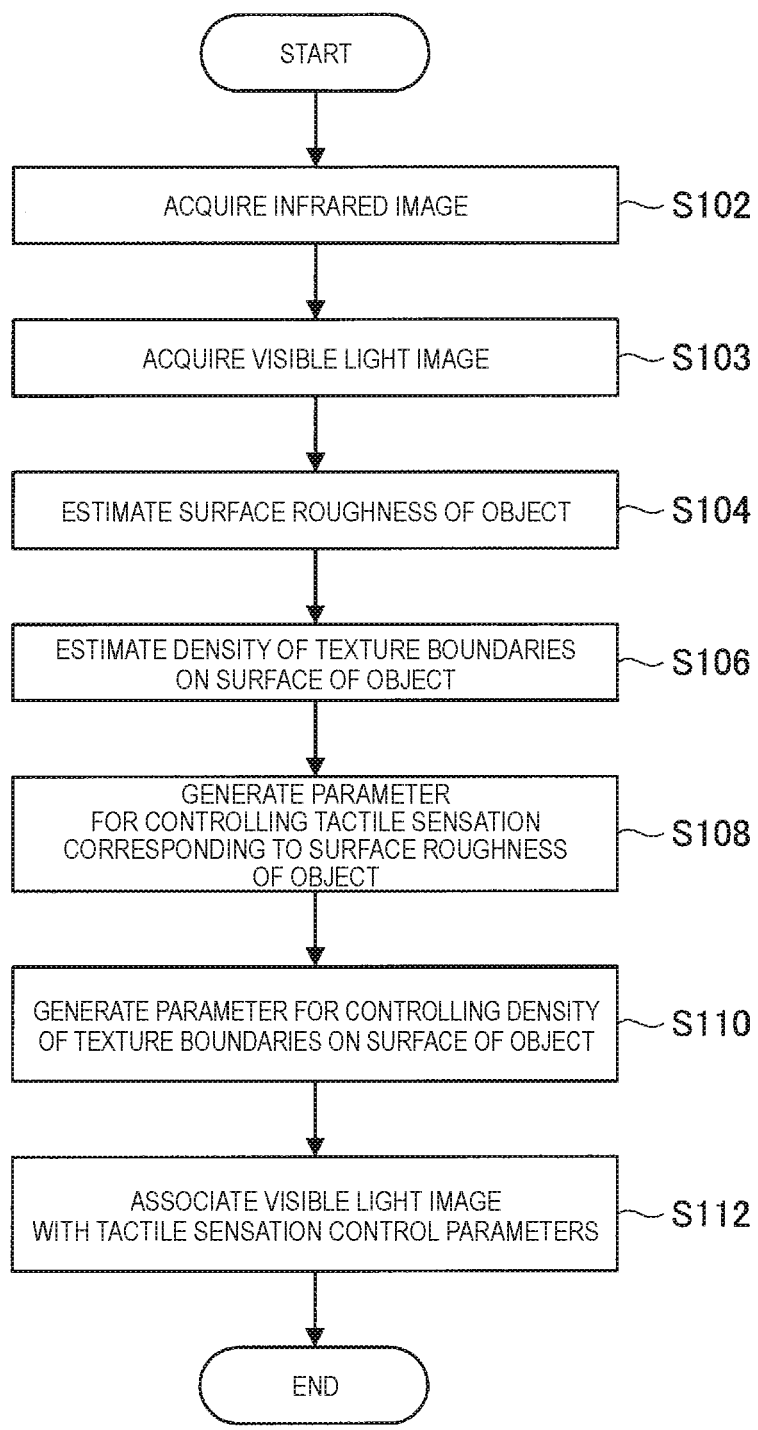
FIG. 12 is a flowchart illustrating a specific example of a flow of processing performed by the image processing device according to the embodiment of the present disclosure.

FIG. 12 is a flowchart illustrating a specific example of a flow of processing performed by the image processing device 10 according to the embodiment of the present disclosure. As illustrated in FIG. 12, the infrared image acquisition unit 152 first acquires infrared images at a plurality of infrared ray irradiation angles (Step S102) and then outputs the acquired plurality of infrared images to the generation unit 158. Then, the visible light image acquisition unit 154 acquires a visible light image (Step S103) and outputs the acquired visible light image to the data processing unit 160. Next, the generation unit 158 estimates a surface roughness of an object on the basis of the plurality of infrared images obtained at the plurality of infrared ray irradiation angles (Step S104). Subsequently, the generation unit 158 estimates a density of texture boundaries on a surface of the object on the basis of the estimated surface roughness of the object (Step S106). Next, the generation unit 158 generates a parameter for controlling a tactile sensation corresponding to the estimated surface roughness of the object (Step S108) and generates a parameter for controlling a tactile sensation corresponding to the estimated density of the texture boundaries on the surface of the object (Step S110). The generated tactile sensation parameters are output to the data processing unit 160. Then, the data processing unit 160 associates the visible light image and the tactile sensation control parameters (Step S112). Then, the processing illustrated in FIG. 12 is completed.

[2-4. Advantages]

According to the aforementioned embodiment, the generation unit 158 generates cutaneous sensation control parameters on the basis of an infrared image input from the infrared image acquisition unit 152, and the data processing unit 160 associates a visible light image acquired by the visible light image acquisition unit 154 with the cutaneous sensation control parameters generated by the generation unit 158. Therefore, it is possible to reduce manual operations in a cutaneous sensation control setting corresponding to images. Therefore, it is possible to reduce a human load in the cutaneous sensation control setting corresponding to images.

Further, according to the aforementioned embodiment, the generation unit 158 generates the cutaneous sensation control parameters for each pixel region of an infrared image, and the data processing unit 160 performs association by assigning the cutaneous sensation control parameters to pixels of a visible light image corresponding to each of the pixel regions of the infrared image. Therefore, it is possible to reduce the cutaneous sensation control parameter generation processing. Therefore, it is possible to increase a speed of the cutaneous sensation control setting.

Further, according to a certain embodiment, the generation unit 158 generates a parameter for controlling a tactile sensation corresponding to a surface roughness of an object and a parameter for controlling a tactile sensation corresponding to a density of texture boundaries on a surface of the object as the tactile sensation control parameters on the basis of pixel values of an infrared image input from the infrared image acquisition unit 152. In this manner, it is possible to reduce a human load in s control setting for the tactile sensation corresponding to the surface roughness of the object and the tactile sensation corresponding to the density of the texture boundaries on the surface of the object corresponding to images.

Further, according to a certain embodiment, the infrared image acquisition unit 152 acquires infrared images at a plurality of infrared ray irradiation angles with respect to an imaged object, and the generation unit 158 generates tactile sensation control parameters on the basis of the plurality of infrared images acquired by the infrared image acquisition unit 152. In this manner, it is possible to generate a likely tactile sensation control parameter corresponding to images by utilizing reflected light intensity properties of a surface of the object with respect to angles of light emitted toward the surface of the object.

Further, according to a certain embodiment, the generation unit 158 generates a parameter for controlling a tactile sensation corresponding to a surface roughness of an object by estimating a surface roughness of the object in each pixel region on the basis of a distribution of pixel values corresponding to the pixel region at a plurality of infrared ray irradiation angles, and generates a parameter for controlling a tactile sensation corresponding to a density of texture boundaries on a surface of the object by estimating the density of the texture boundaries on the surface of the object on the basis of a dispersion estimated surface roughnesses of the object. In this manner, it is possible to generate a likely parameter for controlling a tactile sensation corresponding to the surface roughness of the object and a likely parameter for controlling a tactile sensation corresponding to the density of the texture boundaries on the surface of the object corresponding to images by utilizing reflected light intensity properties of the surface of the object with respect to angles of light emitted toward the surface of the object.

Further, according to a certain embodiment, the generation unit 158 generates a value indicating a frequency of oscillations that are caused in a target as a parameter for controlling a tactile sensation corresponding to a surface roughness of the object, and generates a value indicating a duration time of the oscillations that are caused in the target as a parameter for controlling a tactile sensation corresponding to a density of texture boundaries on a surface of the object on the basis of pixel values of an infrared image input from the infrared image acquisition unit 152. In this manner, it is possible to reduce a human load in a tactile sensation control setting corresponding to images by utilizing oscillation stimulation.

[2-5. Modification Example]

The example in which a value indicating a frequency of oscillations that were caused in the target was generated as a parameter for controlling a tactile sensation corresponding to a surface roughness of the object and a value indicating a duration time of the oscillations that were caused in the target was generated as a parameter for controlling a tactile sensation corresponding to a density of texture boundaries on a surface of the object was described hitherto. The technical scope of the present disclosure is not limited to such an example, and for example, a value of a voltage to be applied to targets is generated as the parameter for controlling a tactile sensation corresponding to the surface roughness of the object, and a value indicating an interval of the targets to which the voltage is applied is generated as the parameter for controlling tactile sensation corresponding to the density of the texture boundaries on the surface of the object in a modification example that will be described below.

Figure 13:
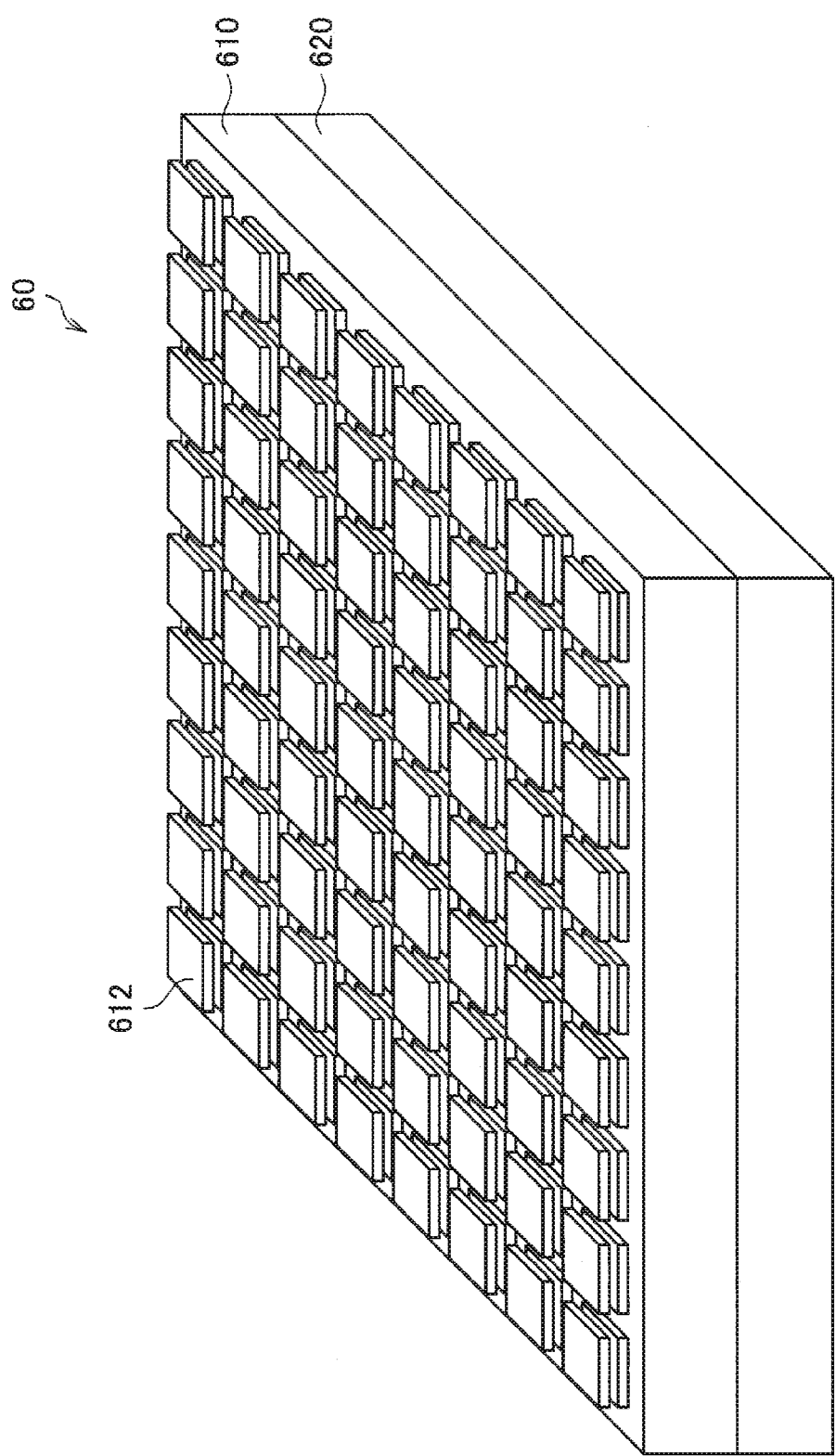
FIG. 13 is an appearance diagram illustrating a second example of the tactile sensation presenting display.

Here, a technology for applying a function of controlling a tactile sensation through electrical stimulation by controlling a voltage to be applied to counter electrodes arranged in a grid shape in a display apparatus that displays images is known (for example, Patent Literature 1). FIG. 13 is an appearance diagram illustrating a specific example of a tactile sensation presenting display 60 using such a technology. As illustrated in FIG. 13, the tactile sensation presenting display 60 includes a tactile sensation presenting unit 610 that includes counter electrodes 612 arranged in a grid shape and a display unit 620 that displays images. The tactile sensation presenting display 60 can control a tactile sensation while displaying images due to the tactile sensation presenting unit 610 being laminated on the display unit 620. Also, it is known that a value of a voltage to be applied to the counter electrodes 612 is correlated with a tactile sensation corresponding to a surface roughness of an object and that an interval of the counter electrodes 612 to which the voltage is applied is correlated with a tactile sensation corresponding to a density of texture boundaries on a surface of the object in the tactile sensation presenting display 60.

In the modification example, the generation unit 158 generates a value of a voltage to be applied to the targets, for example, as the parameter for controlling a tactile sensation corresponding to a surface roughness of the object estimated by the generation unit 158. Also, the generation unit 158 generates a value indicating an interval of the targets to which the voltage is applied, for example, as the parameter for controlling a tactile sensation corresponding to a density of texture boundaries on a surface of the object estimated by the generation unit 158. The generation unit 158 may generate tactile sensation control parameters for each pixel region of an infrared image.

According to the aforementioned certain modification example, the generation unit 158 generates the value of the voltage to be applied to the targets as the parameter for controlling a tactile sensation corresponding to the surface roughness of the object and generates the value indicating the interval of the targets to which the voltage is applied as the parameter for controlling a tactile sensation corresponding to the density of the texture boundaries on the surface of the object. In this manner, it is possible to reduce a human load in a tactile sensation control setting corresponding to images by utilizing electrical stimulation.

[2-6. Application Example]

The example in which tactile sensation control parameters were generated as cutaneous sensation control parameters was described hitherto. The technical scope of the present disclosure is not limited to such an example, and for example, temperature sensation control parameters are generated as cutaneous sensation control parameters in an application example that will be described below.

The generation unit 158 estimates a temperature of an object on the basis of pixel values of infrared image acquired by the infrared image acquisition unit 152. Then, the generation unit 158 generates temperature sensation control parameters on the basis of the estimated temperature of the object.

Specifically, the generation unit 158 estimates the temperature of the object on the basis of pixel values of an infrared image acquired by the infrared image acquisition unit 152 by utilizing a relationship between the temperature of the object and energy of infrared rays emitted from the object. In the application example, the infrared image acquired by the infrared image acquisition unit 152 is mainly an MWIR image or an FIR image. Since emission of infrared rays is not required for capturing an MWIR image or an FIR image, a light emitting element can be omitted from a configuration of the infrared camera 102 according to the application example.

Figure 14:
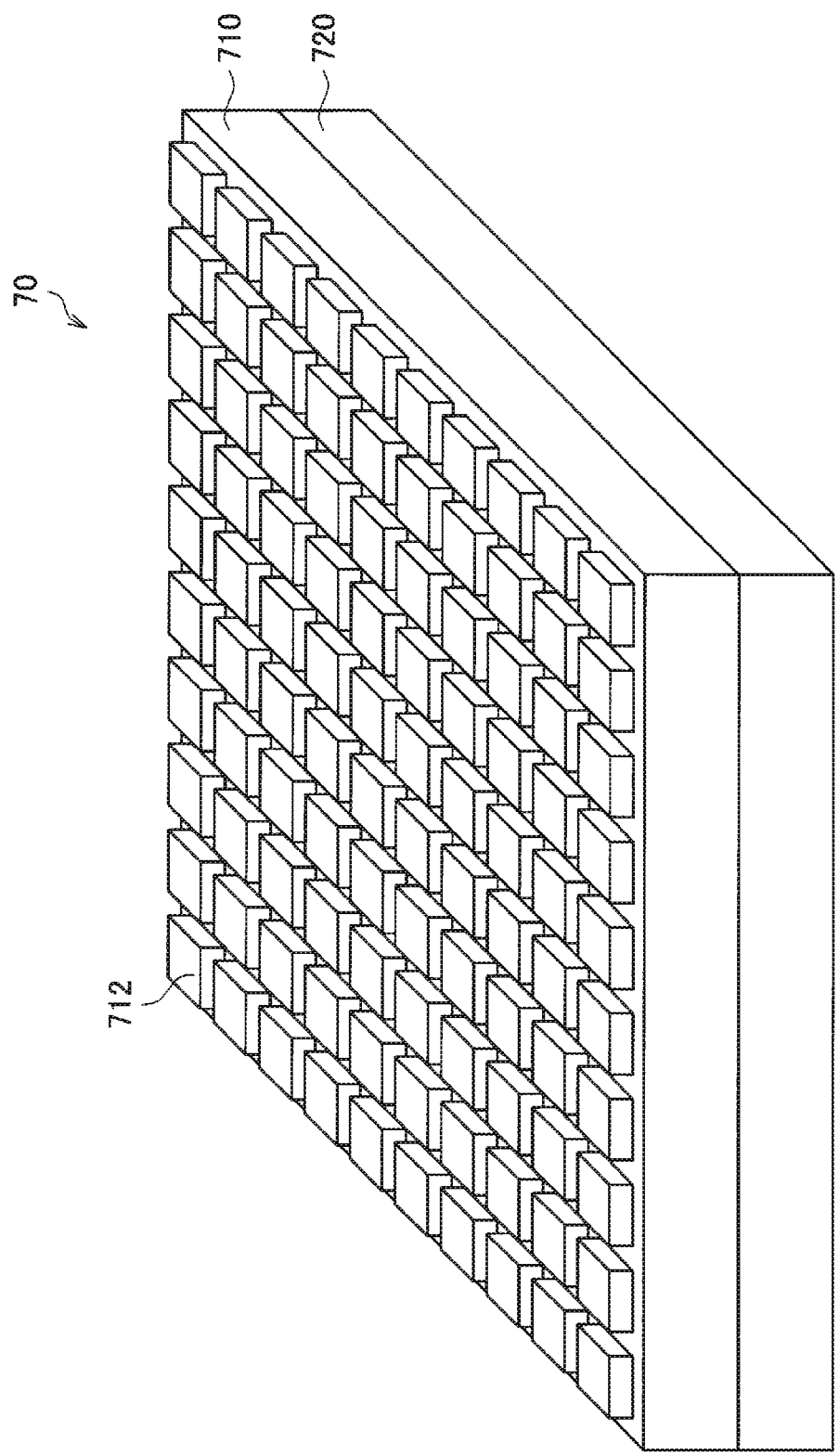
FIG. 14 is an appearance diagram illustrating a specific example of the temperature sensation presenting display.

Here, a technology of controlling a temperature sensation through temperature stimulation by controlling a current to be applied to Peltier devices arranged in a grid shape is known (for example, Patent Literature 2). FIG. 14 is an appearance diagram illustrating a specific example of a temperature sensation presenting display 70 that uses such a technology. As illustrated in FIG. 14, the temperature sensation presenting display 70 includes a temperature sensation presenting unit 710 that includes Peltier devices 712 arranged in a grid shape and a display unit 720 that displays images. The temperature sensation presenting display 70 can control a temperature sensation while displaying images due to the temperature sensation presenting unit 710 being laminated on the display unit 720. Also, it is known that an absolute value and a direction of a current applied to the Peltier devices 712 are correlated with a temperature sensation in the temperature sensation presenting display 70. Specifically, a degree of heating or cooling by the Peltier devices 172 is controlled by the absolute value of the current applied to the Peltier devices 712, and whether to heat or cool the Peltier devices 712 is controlled by a direction of the current applied to the Peltier devices 712.

Figure 15:
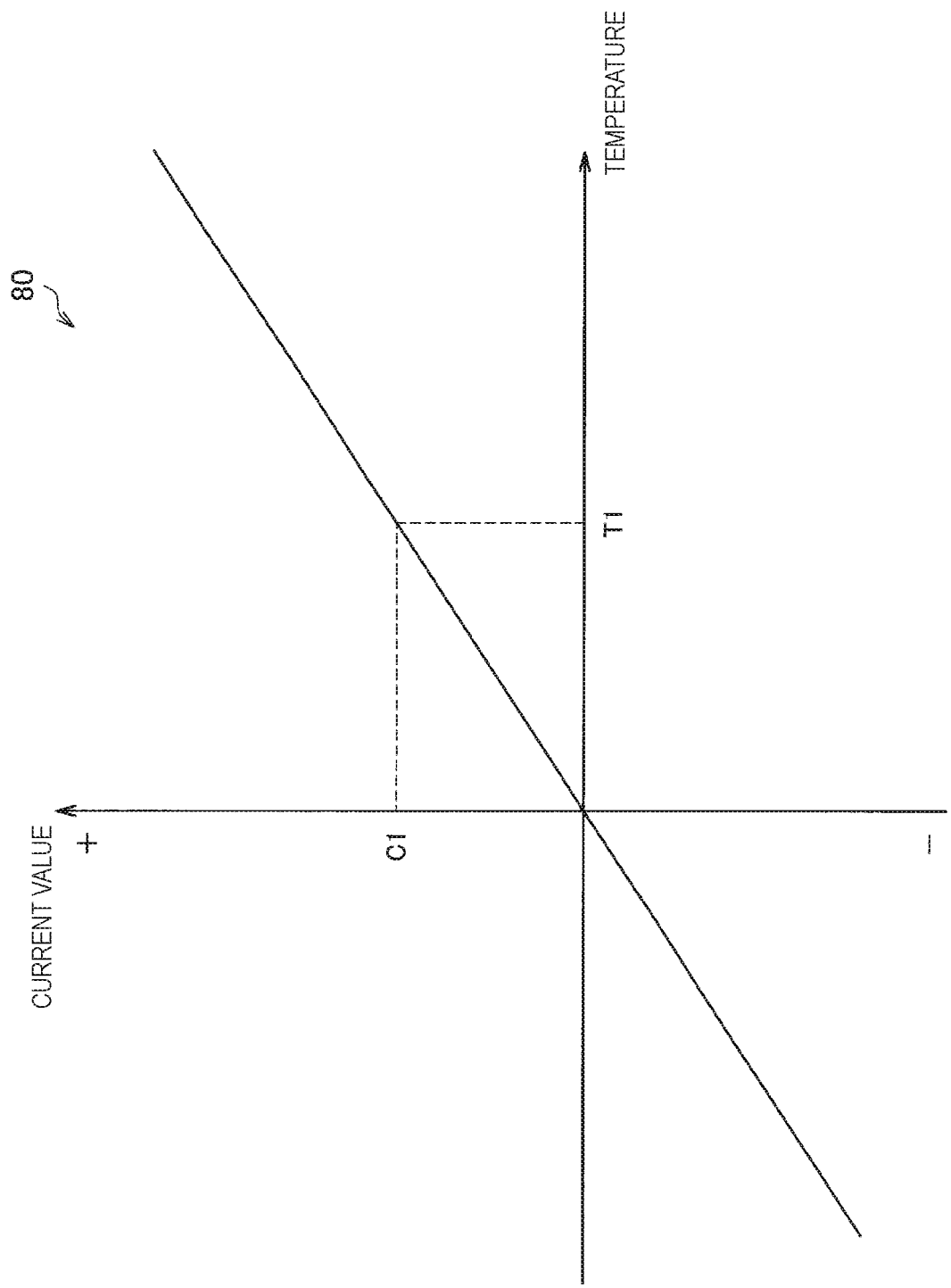
FIG. 15 is an explanatory diagram illustrating a specific example of a correlation model between a temperature of an object and a current value.

In the application example, the generation unit 158 generates values indicating the absolute value and the direction of the current to be applied to the target, for example, as the temperature sensation control parameters. FIG. 15 is an explanatory diagram illustrating a specific example of a correlation model 80 between a temperature of an object and a value of a current. FIG. 15 illustrates a current value corresponding to each temperature of the object. The generation unit 158 acquires the correlation model 80 stored in the storage unit 156 and specifies a current value C1 corresponding to an estimated temperature T1 of the object by using the acquired correlation model 80. Then, the generation unit 158 generates values indicating an absolute value and a direction of the specified current value C1 as temperature sensation control parameters.

Next, a flow of processing performed by the image processing device 10 according to the application example will be described with reference to FIG. 16.

Figure 16:
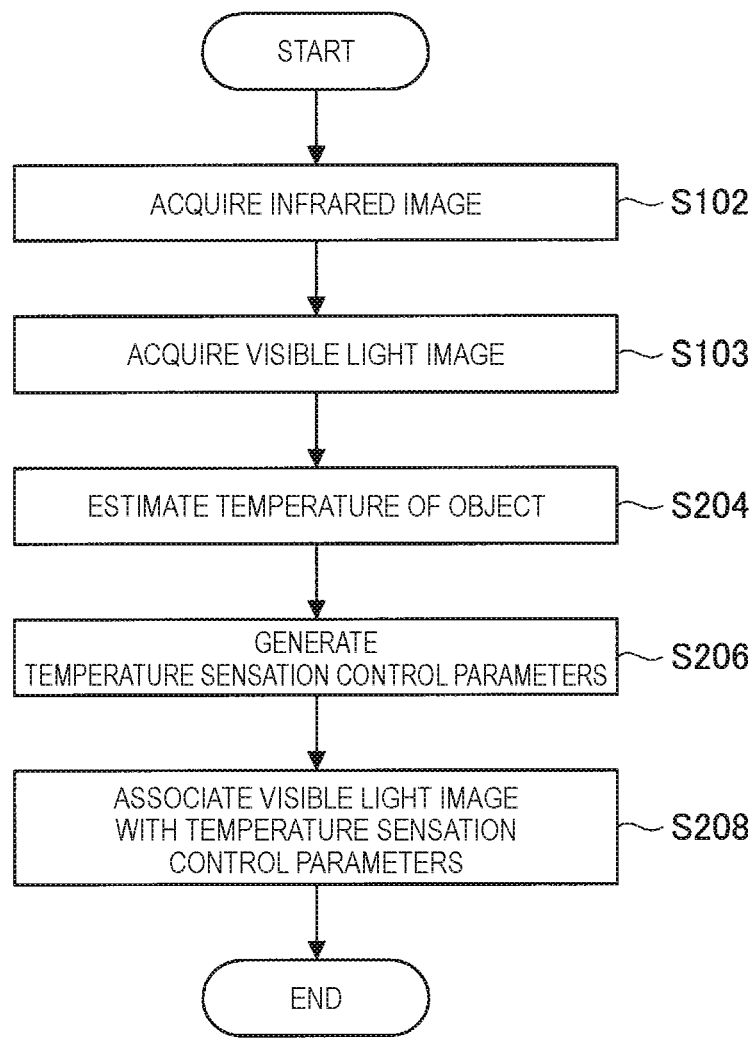
FIG. 16 is a flowchart illustrating a specific example of a flow of processing performed by an image processing device according to an application example.

FIG. 16 is a flowchart illustrating a specific example of the flow of the processing performed by the image processing device 10 according to the application example. As illustrated in FIG. 16, the infrared image acquisition unit 152 output an infrared image to the generation unit 158, and the generation unit 158 then estimates a temperature of an object on the basis of the infrared image input from the infrared image acquisition unit 152 (Step S204). Subsequently, the generation unit 158 generates parameters for controlling a temperature sensation on the basis of the estimated temperature of the object (Step S206) and outputs the generated temperature sensation control parameter to the data processing unit 160. Then, the data processing unit 160 associates a visible light image and the temperature sensation control parameter (Step S208). Then, the processing illustrated in FIG. 16 is completed.

According to the aforementioned certain application example, the generation unit 158 generates temperature sensation control parameters on the basis of pixel values of an infrared image acquired by the infrared image acquisition unit 152. In this manner, it is possible to reduce a human load in temperature sensation control setting corresponding to images.

According to the aforementioned certain application example, the generation unit 158 generates the values indicating the absolute value and the direction of the current to be applied to the target as the temperature sensation control parameters. In this manner, it is possible to reduce a human load in temperature sensation control setting corresponding to images by utilizing the current.

<3. Conclusion>

According to the embodiment of the present disclosure, cutaneous sensation control parameters are generated on the basis of an acquired infrared image, and an acquired visible light image is associated with the generated cutaneous sensation control parameters as described above. Therefore, it is possible to reduce manual operations in a cutaneous sensation control setting corresponding to images. Therefore, it is possible to reduce a human load in the cutaneous sensation control setting corresponding to images.

Also, the cutaneous sensation control parameters are generated for each pixel region of an infrared image, and association is performed by assigning the cutaneous sensation control parameters to pixels of a visible light image corresponding to each of the pixel regions of the infrared image according to the embodiment of the present disclosure. Therefore, it is possible to reduce cutaneous sensation control parameter generation processing. Therefore, it is possible to increase a speed of the cutaneous sensation control setting.

Further, according to a certain embodiment, a parameter for controlling a tactile sensation corresponding to a surface roughness of an object and a parameter for controlling a tactile sensation corresponding to a density of texture boundaries on a surface of the object are generated as tactile sensation control parameters on the basis of pixel values of an acquired infrared image. In this manner, it is possible to reduce a human load in a control setting for a tactile sensation corresponding to the surface roughness of the object and a tactile sensation corresponding to the density of the texture boundaries on the surface of the object corresponding to images.

Further, according to a certain embodiment, infrared images are acquired at a plurality of infrared ray irradiation angles with respect to an imaged object, and tactile sensation control parameters are generated on the basis of the acquired plurality of infrared images. In this manner, it is possible to generate likely tactile sensation control parameters corresponding to the images by utilizing reflected light intensity properties of a surface of the object with respect to angles of light emitted toward the surface of the object.

Further, according to a certain embodiment, a parameter for controlling a tactile sensation corresponding to a surface roughness of an object and a parameter for controlling a tactile sensation corresponding to a density of texture boundaries on a surface of the object are generated on the basis of pixel values of an acquired infrared image. In this manner, it is possible to reduce a human load in a control setting for a tactile sensation corresponding to the surface roughness of the object and a tactile sensation corresponding to the density of the texture boundaries on the surface of the object corresponding to images.

Further, according to a certain embodiment, a parameter for controlling a tactile sensation corresponding to a surface roughness of an object is generated by estimating the surface roughness of the object in a pixel region on the basis of a distribution of pixel values corresponding to the pixel region at a plurality of infrared ray irradiation angles, and a parameter for controlling a tactile sensation corresponding to a density of texture boundaries on a surface of the object is generated by estimating the density of the texture boundaries on the surface of the object on the basis of a dispersion of estimated surface roughnesses of the object. In this manner, it is possible to generate a likely parameter for controlling a tactile sensation corresponding to the surface roughness of the object and a likely parameter for controlling a tactile sensation corresponding to the density of the texture boundaries on the surface of the object corresponding to images by utilizing reflected light intensity properties of the surface of the object with respect to angles of light emitted toward the surface of the object.

Further, according to a certain embodiment, a value indicating a frequency of oscillations that are caused in a target is generated as a parameter for controlling a tactile sensation corresponding to a surface roughness of the object, and a value indicating a duration time of the oscillations that are caused in the target is generated as a parameter for controlling a tactile sensation corresponding to a density of texture boundaries on a surface of the object on the basis of pixel values of an acquired infrared image. In this manner, it is possible to reduce a human load in a tactile sensation control setting corresponding to images by utilizing oscillation stimulation.

Further, according to a certain modification example, a value of a voltage to be applied to targets is generated as a parameter for controlling a tactile sensation corresponding to a surface roughness of the object, and a value indicating an interval of the targets to which the voltage is applied is generated as a parameter for controlling a tactile sensation corresponding to a density of texture boundaries on a surface of the object. In this manner, it is possible to reduce a human load in a tactile sensation control setting corresponding to images by utilizing electrical stimulation.

Further, according to a certain application example, temperature sensation control parameters are generated on the basis of pixel values of an acquired infrared image. In this manner, it is possible to reduce a human load in a temperature sensation control setting corresponding to images.

Further, according to a certain application example, values indicating an absolute value and a direction of a current to be applied to a target are generated as temperature sensation control parameters. In this manner, it is possible to reduce a human load in a temperature sensation control setting corresponding to images by utilizing a current.

The series of control processes carried out by each apparatus described in the present specification may be realized by software, hardware, or a combination of software and hardware. Programs that compose such software may be stored in advance for example on a storage medium (non-transitory medium) provided inside or outside each of the apparatus. As one example, during execution by a computer, such programs are written into RAM (Random Access Memory) and executed by a processor such as a CPU.

Note that it is not necessary for the processing described in this specification with reference to the flowchart to be executed in the order shown in the flowchart. Some processing steps may be performed in parallel. Further, some of additional steps can be adopted, or some processing steps can be omitted.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An image processing device including:
an infrared image acquisition unit that acquires an infrared image of an imaged object;
a visible light image acquisition unit that acquires a visible light image of the imaged object;
a generation unit that generates cutaneous sensation control parameters on the basis of the infrared image acquired by the infrared image acquisition unit; and
a data processing unit that associates the visible light image acquired by the visible light image acquisition unit with the cutaneous sensation control parameters generated by the generation unit.

(2)

The image processing device according to (1),
in which the generation unit generates the cutaneous sensation control parameters for each pixel region of the infrared image, and
the data processing unit performs the association by assigning the cutaneous sensation control parameters to pixels of the visible light image that correspond to each pixel region of the infrared image.

(3)

The image processing device according to (2),
in which the cutaneous sensation control parameters include tactile sensation control parameters, and
the generation unit generates the tactile sensation control parameters on the basis of pixel values of the infrared image acquired by the infrared image acquisition unit.

(4)

The image processing device according to (3),
in which the infrared image acquisition unit acquires infrared images at a plurality of infrared ray irradiation angles with respect to the imaged object, and
the generation unit generates the tactile sensation control parameters on the basis of the plurality of infrared images acquired by the infrared image acquisition unit.

(5)

The image processing device according to (4),
in which the tactile sensation control parameters include a parameter for controlling a tactile sensation corresponding to a surface roughness of an object and a parameter for controlling a tactile sensation corresponding to a density of texture boundaries on a surface of the object.

(6)

The image processing device according to (5),
in which the generation unit generates the parameter for controlling a tactile sensation corresponding to the surface roughness of the object by estimating a surface roughness of the object in the pixel region on the basis of a distribution of pixel values corresponding to the pixel region at the plurality of infrared ray irradiation angles, and generates the parameter for controlling a tactile sensation corresponding to the density of the texture boundaries on the surface of the object by estimating the density of the texture boundaries on the surface of the object on the basis of a dispersion of estimated surface roughnesses of the object.

(7)

The image processing device according to (5) or (6),
in which the parameter for controlling a tactile sensation corresponding to the surface roughness of the object includes a value indicating a frequency of an oscillation that is caused in a target, and
the parameter for controlling a tactile sensation corresponding to the density of the texture boundaries on the surface of the object includes a value indicating a duration time of the oscillation.

(8)

The image processing device according to (5) or (6),
in which the parameter for controlling a tactile sensation corresponding to the surface roughness of the object includes a value of a voltage applied to targets, and
the parameter for controlling a tactile sensation corresponding to the density of the texture boundaries on the surface of the object includes a value indicating an interval of the targets to which the voltage is applied.

(9)

The image processing device according to (2),
in which the cutaneous sensation control parameters include temperature sensation control parameters, and
the generation unit generates the temperature sensation control parameters on the basis of pixel values of the infrared image acquired by the infrared image acquisition unit.

(10)

The image processing device according to (9),
in which the temperature sensation control parameters include an absolute value of a current applied to a target and a value indicating a direction of the current.

(11)

An image processing method including:
acquiring an infrared image of an imaged object by an image processing device;
acquiring a visible light image of the imaged object;
generating cutaneous sensation control parameters on the basis of the acquired infrared image; and
associating the acquired visible light image with the generated cutaneous sensation control parameters.

(12)

A program causing a computer that controls an image processing device to function as:
an infrared image acquisition unit that acquires an infrared image of an imaged object;
a visible light image acquisition unit that acquires a visible light image of the imaged object;
a generation unit that generates cutaneous sensation control parameters on the basis of the infrared image acquired by the infrared image acquisition unit; and
a data processing unit that associates the visible light image acquired by the visible light image acquisition unit with the cutaneous sensation control parameters generated by the generation unit.

REFERENCE SIGNS LIST 10 image processing device
40 tactile sensation presenting display
60 tactile sensation presenting display
70 temperature sensation presenting display
102 infrared camera
104 visible light camera
106 input interface
108 memory
112 communication interface
114 storage
116 processor
118 bus
152 infrared image acquisition unit
154 visible light image acquisition unit
156 storage unit
158 generation unit
160 data processing unit
410, 610 tactile sensation presenting unit
412 oscillator
420, 620, 720 display unit
612 counter electrode
710 temperature sensation presenting unit
712 Peltier device

The invention claimed is:

1. An image processing device, comprising:
an infrared image acquisition unit configured to acquire a plurality of infrared images at a plurality of infrared ray irradiation angles with respect to an imaged object;
a visible light image acquisition unit configured to acquire a visible light image of the imaged object, wherein
each pixel region of a plurality of pixel regions of an infrared image of the plurality of infrared images corresponds to a set of pixels of the visible light image;
a generation unit configured to:
estimate a surface roughness of the imaged object in each pixel region of the plurality of pixel regions based on a distribution of pixel values corresponding to each pixel region of the plurality of pixel regions at the plurality of infrared ray irradiation angles;
generate a first parameter of a plurality of cutaneous sensation control parameters based on the estimated surface roughness of the imaged object and pixel values of the plurality of infrared images;
estimate a density of texture boundaries on a surface of the imaged object based on a dispersion of the estimated surface roughness of the imaged object; and
generate a second parameter of the plurality of cutaneous sensation control parameters based on the estimated density of the texture boundaries on the surface of the imaged object and the pixel values of the plurality of infrared images, wherein
the plurality of cutaneous sensation control parameters includes tactile sensation control parameters, and
the tactile sensation control parameters include the first parameter to control a first tactile sensation corresponding to the surface roughness of the imaged object, and the second parameter to control a second tactile sensation corresponding to the density of the texture boundaries on the surface of the imaged object; and a data processing unit configured to assign the plurality of cutaneous sensation control parameters to the set of pixels of the visible light image.

2. The image processing device according to claim 1, wherein
the first parameter includes a value that indicates a frequency of an oscillation of a target, and
the second parameter includes a value that indicates a duration time of the oscillation.

3. The image processing device according to claim 1, wherein
the first parameter includes a value of a voltage applied to targets, and
the second parameter includes a value that indicates an interval of the targets.

4. The image processing device according to claim 1, wherein
the plurality of cutaneous sensation control parameters further includes temperature sensation control parameters, and
the generation unit is further configured to generate the temperature sensation control parameters based on the pixel values of the plurality of infrared images.

5. The image processing device according to claim 4, wherein
the temperature sensation control parameters include an absolute value of a current applied to a target and a value indicating a direction of the current.

6. An image processing method, comprising:
acquiring, by an image processing device, a plurality of infrared images at a plurality of infrared ray irradiation angles with respect to an imaged object;
acquiring, by the image processing device, a visible light image of the imaged object, wherein
each pixel region of a plurality of pixel regions of an infrared image of the plurality of infrared images corresponds to a set of pixels of the visible light image;
estimating, by the image processing device, a surface roughness of the imaged object in each pixel region of the plurality of pixel regions based on a distribution of pixel values corresponding to each pixel region of the plurality of pixel regions at the plurality of infrared ray irradiation angles;
generating, by the image processing device, a first parameter of a plurality of cutaneous sensation control parameters based on the estimated surface roughness of the imaged object and pixel values of the plurality of infrared images;
estimating, by the image processing device, a density of texture boundaries on a surface of the imaged object based on a dispersion of the estimated surface roughness of the imaged object;
generating, by the image processing device, a second parameter of the plurality of cutaneous sensation control parameters based on the estimated density of the texture boundaries on the surface of the imaged object and the pixel values of the plurality of infrared images, wherein
the plurality of cutaneous sensation control parameters includes tactile sensation control parameters, and
the tactile sensation control parameters include the first parameter to control a first tactile sensation corresponding to the surface roughness of the imaged object, and the second parameter to control a second tactile sensation corresponding to the density of the texture boundaries on the surface of the imaged object; and assigning, by the image processing device, the plurality of cutaneous sensation control parameters to the set of pixels of the visible light image.

7. A non-transitory computer-readable medium having stored thereon computer-executable instructions, which when executed by a processor of an image processing device, cause the processor to execute operations, the operations comprising:

acquiring a plurality of infrared images at a plurality of infrared ray irradiation angles with respect to an imaged object;

acquiring a visible light image of the imaged object, wherein
each pixel region of a plurality of pixel regions of an infrared image of the plurality of infrared images corresponds to a set of pixels of the visible light image;

estimating a surface roughness of the imaged object in each pixel region of the plurality of pixel regions based on a distribution of pixel values corresponding to each pixel region of the plurality of pixel regions at the plurality of infrared ray irradiation angles;

generating a first parameter of a plurality of cutaneous sensation control parameters based on the estimated surface roughness of the imaged object and pixel values of the plurality of infrared images;

estimating a density of texture boundaries on a surface of the imaged object based on a dispersion of the estimated surface roughness of the imaged object;

generating a second parameter of the plurality of cutaneous sensation control parameters based on the estimated density of the texture boundaries on the surface of the imaged object and the pixel values of the plurality of infrared images, wherein
the plurality of cutaneous sensation control parameters includes tactile sensation control parameters, and
the tactile sensation control parameters include the first parameter to control a first tactile sensation corresponding to the surface roughness of the imaged object, and the second parameter to control a second tactile sensation corresponding to the density of the texture boundaries on the surface of the imaged object; and assigning the plurality of cutaneous sensation control parameters to the set of pixels of the visible light image.

* * * * *